United States Patent
Dekany et al.

(10) Patent No.: US 12,054,462 B2
(45) Date of Patent: Aug. 6, 2024

(54) SPHINGOSINE/SPHINGOID BASE PRODUCTION

(71) Applicant: CarboCode S.A., Cantanhede (PT)

(72) Inventors: Gyula Dekany, Sinnamon Park (AU); Ferenc Horvath, Pilisszentkereszt (HU); Györgyi Osztrovszky, Kisvarda (HU); Jorge Santos, Alenquer (PT); Piroska Kovacs-Penzes, Jaszbereny (HU); Andras Nagy, Komlo (HU)

(73) Assignee: CarboCode S.A., Cantanhede (PT)

( * ) Notice: Subject to any disclaimer, the term of this patent is extended or adjusted under 35 U.S.C. 154(b) by 830 days.

(21) Appl. No.: 17/251,978

(22) PCT Filed: Jun. 14, 2019

(86) PCT No.: PCT/EP2019/065785
§ 371 (c)(1),
(2) Date: Dec. 14, 2020

(87) PCT Pub. No.: WO2019/238970
PCT Pub. Date: Dec. 19, 2019

(65) Prior Publication Data
US 2021/0253536 A1    Aug. 19, 2021

(30) Foreign Application Priority Data
Jun. 15, 2018 (DE) ............... 10 2018 114 379.6

(51) Int. Cl.
C07D 239/60    (2006.01)
C07C 213/08    (2006.01)

(52) U.S. Cl.
CPC .......... *C07D 239/60* (2013.01); *C07C 213/08* (2013.01)

(58) Field of Classification Search
CPC ... C07D 239/60; C07C 213/08; C07C 215/24; Y02P 20/55
USPC ...................................... 544/301
See application file for complete search history.

(56) References Cited

U.S. PATENT DOCUMENTS 6,462,183 B1    10/2002 Toth et al.
2003/0171621 A1  9/2003 Van Boom et al.

FOREIGN PATENT DOCUMENTS

EP    1452520 A1    9/2004
WO    9838197 A1    9/1998

OTHER PUBLICATIONS

Chaudhari et al., "An Efficient Synthesis of D-erythro- and D-threo-Sphingosine from d-Glucose: Olefin Cross-Metathesis Approach", Org. Lett., 2005, pp. 5805-5807, vol. 7, No. 26.
Dekany et al., "A novel amino protecting group: DTPM", Tetrahedron Letters, 2001, pp. 3129-3132, vol. 42, No. 17.
Di Benedetto et al., "Protected sphingosine from phytosphingosine as an efficient acceptor in glycosylation reaction", Org. Lett., 2014, pp. 952-955, vol. 16, No. 3.
Abraham et al., "Asymmetric synthesis of vicinal amino alcohols: xestoaminol C, sphinganine and sphingosine", Org. Biomol. Chem., 2008, pp. 1655-1664, vol. 6.
Gao et al., "Recent progress in chemical syntheses of sphingosines and phytosphingosines", Synthesis, 2016, pp. 4017-4037, vol. 48, No. 23.
Ha et al., "Synthesis of D-erythro-Sphingosine from D-ribo-Phytosphingosine", Bull. Korean Chem. Soc., 2009, pp. 535-536, vol. 30, No. 3.
Kim et al., "Efficient Synthesis of D-erythro-Sphingosine and D-erythro-Azidosphingosine from D-ribo-Phytosphingosine via a Cyclic Sulfate Intermediate", J. Org. Chem., 2006, pp. 8661-8664, vol. 71, No. 22.
Llaveria et al., "An efficient and general enantioselective synthesis of sphingosine, phythosphingosine, and 4-substituted derivatives", Org. Lett., 2009, pp. 205-208, vol. 11, No. 1.
Merino et al., "Enantiodivergent Synthesis of d- and I-e rythro-Sphingosines through Mannich-Type Reactions of N-Benzyl-2,3-O-isopropylidene-d-glyceraldehyde Nitrone", J.Org. Chem., 2006, pp. 4685-4688, vol. 71, No. 12.
Morales-Serna et al., "Synthesis of D/L-erythro-Sphingosine Using a Tethered Aminohydroxylation Reaction as the Key Step", Synthesis, 2009, pp. 710-712, vol. 5.
Murakami et al., "Regio- and stereocontrolled synthesis of d-erythro-sphingosine and phytosphingosine from d-glucosamine", Tetrahedron Lett., 1994, pp. 745-748, vol. 35, No. 5.

(Continued)

*Primary Examiner* — Taylor V Oh
(74) *Attorney, Agent, or Firm* — Neal, Gerber & Eisenberg LLP

(57) ABSTRACT

The present invention relates to sphingolipids, a method for the production of sphingoid bases, especially sphingosine, and novel derivatives thereof. The sphingoid bases are herein produced by making use of a vinylogous amide-type protecting group. The resulting vinylogous amide compounds enable an easy and effective production of sphingoid bases, especially sphingosine.

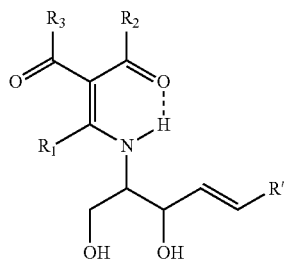

General Formula VII

13 Claims, No Drawings

(56) References Cited

OTHER PUBLICATIONS

Shinozaki et al., "Synthesis of D-erythro-Sphingosine from D-Glucosamine", Chem. Pharm. Bull., 1996, pp. 927-932, vol. 44, No. 5.

Sridhar et al., "Asymmetric synthesis of triacetyl-d-erythro-sphingosine and D-1-deoxyallonojirimycin via Miyashita C2 selective endo-mode azide opening of 2,3-epoxy alcohol", Tetrahedron, 2009, pp. 10701-10708, vol. 65, No. 51.

Van den Berg et al., "A simple and low cost synthesis of D-erythro-sphingosine and D-erythro-azidosphingosine from D-ribo-phytosphingosine: glycosphingolipid precursors", Tetrahedron Lett., 2002, pp. 8409-8412, vol. 43, No. 46.

Van den Berg et al., "Effective, High-Yielding, and Stereospecific Total Synthesis of D-erythro-(2 R, 3 S)-Sphingosine from D-ribo-(2 S, 3 S, 4 R)-Phytosphingosine", J. Org. Chem., 2004, pp. 5699-5704, vol. 69, No. 17.

Wild et al., "Sphingosine and phytosphingosine from D-threose synthesis of a 4-keto-ceramide", Tetrahedron: Asymmetry, 1994, pp. 2195-2208, vol. 5, No. 11.

Wisse et al., "Synthesis of 6-Hydroxysphingosine and α-Hydroxy Ceramide Using a Cross-Metathesis Strategy", J. Org. Chem., 2015, pp. 7258-7265, vol. 80, No. 14.

Yang et al., "A Concise and Scalable Synthesis of High Enantiopurity (−)-D-erythro-Sphingosine Using Peptidyl Thiol Ester-Boronic Acid Cross-Coupling", Org. Lett., 2007, pp. 2993-2995, vol. 9, No. 16.

Morales-Serna et al., "Recent advances in the glycosylation of sphingosines and ceramides", Carbohydrate Research, 2007, pp. 1595-1612, vol. 342.

Rich et al., "Glycosphingolipid synthesis employing a combination of recombinant glycosyltransferases and an endoglycoceramidase glycosynthase", Chem. Commun., 2011, pp. 10806-10808, vol. 47.

Santra et al., "Highly efficient chemoenzymatic synthesis and facile purification of α-Gal pentasaccharyl ceramide Galα3nLc4βCer", Chemical Communications (Camb), 2017, pp. 8280-8283, vol. 53, No. 59.

SPHINGOSINE/SPHINGOID BASE PRODUCTION

CROSS-REFERENCE TO RELATED APPLICATIONS

This application is the United States national phase of International Application No. PCT/EP2019/065785 filed Jun. 14, 2019, and claims priority to German Patent Application No. 10 2018 114 379.6 filed Jun. 15, 2018, the disclosures of each of which are hereby incorporated by reference in their entireties.

BACKGROUND OF THE INVENTION

Field of the Invention

The present invention relates to sphingolipids, and more particularly to a method for the production of sphingoid bases, especially sphingosine, and novel derivatives thereof. Related Art Sphingolipids are important structural components of plasma and organelle membranes of essentially all eukaryotic cells and play critical roles in many biological processes. They are distributed widely in plants, mammals and microbes. Sphingolipids constitute a diverse group of complex membrane lipids, all containing a long-chain aliphatic amino alcohol, usually having 18 carbons, connected by an amide linkage to a fatty acid to form ceramides. However, sphingoid bases having longer or shorter alkyl chains are also well-known constituents of sphingolipids of eukaryotic life. Sphingoid bases themselves, their O-glycosylated and O-phosphorylated forms, their N-acylated forms, furthermore their substituted/unsubstituted ceramide forms are the most abandoned sphingoid base molecules in nature. Phytoceramides, ceramides, dihydroceramides and 6-hydroxy-ceramides are the most significant ceramide structures in humans carrying phytosphingosine, sphingosine, dihydrosphingosine and 6-hydroxy-sphingosine, respectively. These different ceramide molecules are often referred to as ceramides. Ceramides are usually further modified in life chemistries by enzymatic cascades yielding phosphosphingolipids, glycosylinositol phosphoceramides, glycosphingolipids and their intermediates/metabolites. Sphingolipids—especially glycosphingolipids— have structural and biological functions in maintaining cell membrane integrity, controlling cell growth, apoptosis, signal transduction, etc. by acting as the main components of lipid rafts.

In recent years, a large number of sphingolipid molecules have been gaining interest for nutritional, cosmetic and therapeutic applications due to their high biological activities, excellent pharmacokinetics and their presence in human milk. However, access to human identical sphingolipids and their precursors/metabolites has been prevented by the lack of enabling synthetic production technologies.

For decades, sphingolipid products commercialized mainly for pharmaceutical applications were obtained by extraction of animal brains, especially mammalian brains. However, the obtained sphingolipids were heterogenous mixtures of structurally different sphingolipids, which were potentially unsafe due to the possible presence of hazardous prion, viral and other microbiological entities. Besides this, extraction and subsequent purification of sphingolipids from animal brain tissues is a laborious and expensive method, characterized by non-human chemical structures, low yields and undesired structural diversities. In order to meet the growing demand for sphingolipids, numerous attempts have been made to develop synthetic pathways for producing sphingolipids and their sphingoid base building blocks. One of the important factors for the successful synthesis of natural and non-natural sphingolipids is the synthetic access of the appropriate sphingoid bases, which are the principal backbones of sphingolipids.

Among naturally occurring sphingoid bases, D-erythro-sphingosine (CAS: 123-78-4; $C_{18}H_{37}NO_2$) (1), D-ribo-phytosphingosine (CAS: 388566-94-7; $C_{18}H_{39}NO_3$) (2), DL-erythro-Dihydrosphingosine (CAS: 3102-56-5; $C_{18}H_{39}NO_2$) (3) and 6-Hydroxy-D-erythro-sphingosine (CAS: 566203-07-4; $C_{18}H_{37}NO_3$) (4) are the most important and common species. D-ribo-Phytosphingosine is readily obtainable on industrial scale from a yeast fermentation process. D-erythro-sphingosine is the naturally active configuration of sphingosine and is rather expensive and available only from laborious animal tissue extraction or chemical synthesis.

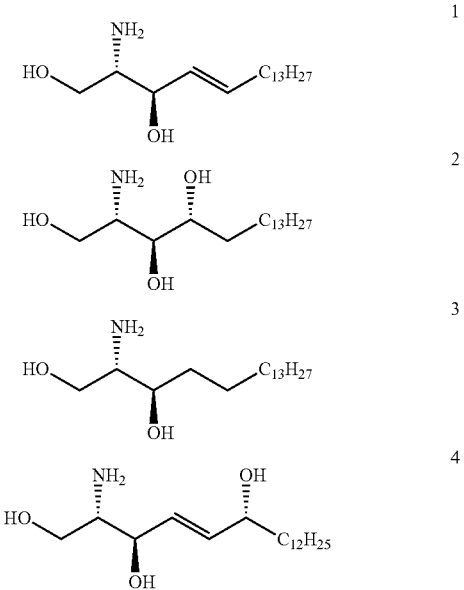

A great deal of effort has been devoted to the synthesis of sphingoid bases, especially of D-erythro-sphingosine 1. To maintain the absolute stereochemistry of the $C_4$-$C_5$-double bond of D-erythro-sphingosine 1 and 6-Hydroxy-D-erythro-sphingosine 4, many synthetic approaches have been tested by using a diverse molecular pool for chirality and related methods such as Sharpless asymmetric epoxidation and asymmetric aldol reaction. Examples are disclosed, for example, in (a) R. Sridhar et. al. *Tetrahedron* 2009, 65 (51), 10701-10708 (b) S. G. Davis et. al. *Org. Biomol. Chem.* 2008, 6, 1655-1664 (c) P. Merino et. al. *J. Org. Chem.* 2006, 71(12), 4685-4688 (d) S. Castellion et. al. *Synthesis.* 2009, 5, 710-712. S. Castillon et. al. *Org. Lett.* 2009, 11(1), 205-208 describes a method for the synthesis of D-erythro-sphingosine from butadiene monoepoxide by a synthetic sequence involving enantioselective allylic substitution, cross-metathesis, and dihydroxylation.

A second popular approach involves the use of chiral starting materials, such as carbohydrates and amino acids.

A large number of approaches have been explored regarding to chiral precursors and carbon-chain elongation methods which have recently been reviewed *Synthesis* 2016; 48(23): 4017-4037. The following entries are provided as examples to show the most typical synthetic efforts made to solve the synthetic challenges of human sphingoid bases, particularly D-erythro-sphingosine 1 and 6-Hydroxy-D-erythro-sphingosine 4 synthesis: D-erythro-sphingosine has been synthesized starting from D-glucosamine in T. Murakami et. al. *Tetrahedron Lett.* 1994, 35(5), 745-748 and Y. Masaki et. al. *Chem. Pharm. Bull.* 1996, 44(5), 927-932, respectively.

R. Wil et. al. *Tetrahedron Asymmetry*, 1994, 2195-2208 describes a stereoselective protocol using D-galactose as a starting material.

In D. D. Dhavale et. al. *Org. Lett.* 2005, 7(26), 5805-5807 a method is disclosed for the preparation of D-erythro-sphingosine 1 from D-glucose via olefin cross metathesis.

In L. S. Liebeskind et. al. *Org. Lett.* 2007, 9(16), 2993-2996 a concise total synthesis of high enantiopurity of D-erythro-sphingosine 1 is revealed starting from N-Boc-L-serine.

P. Wisse et al. *J. Org. Chem.* 2015, DOI: 10.1021/acs.joc.5b00823, describe the synthesis of 6-Hydroxysphingosine and alpha-Hydroxy Ceramide using a cross-metathesis strategy.

All these chemical synthetic routes have in common that the synthetic paths involve a large number of reaction steps, which often provide low yields, low trans/cis selectivities of the required olefinic bond and low stereospecificities. Most importantly, the described methods do not offer robust technologies and scale-up opportunities for the large-scale production of sphingoid bases, especially D-erythro-sphingosine 1.

The relatively inexpensive D-ribo-phytosphingosine 2 has also been employed as a starting material for the synthesis of D-erythro-sphingosine 1. A number of protecting group strategies have been described involving different steps such as azide formation, silylation, oxidation, sulfonylation, cyclic sulfate formation for the regio- and stereoselective transformation of the C-4 hydroxyl group of D-ribo-phytosphingosine 2 into the characteristic 4,5-trans double bond of D-erythro-sphingosine 1. Methods are disclosed, for example, in (a) J. H. van Boom et al. *Tetrahedron Lett.* 2002, 43(46), 8409-8412 (b) J. H. van Boom et. al. *J. Org. Chem.* 2004, 69(17), 5699-5704 (c) H.-J. Ha et. al. *Bull. Korean Chem. Soc.* 2009, 30(3), 535-536 (d) S. Kim et. al. *J. Org. Chem.* 2006, 71(22), 8661-8664 (e) L. Panza et. al. *Org. Lett.* 2014, 16, 952-955.

However, these methods also comprise numerous reaction steps and lack of straightforward purification opportunities via crystallization. Additionally, a number of methods require expensive, special reagents as well as extreme reaction conditions. Therefore, these processes are not suitable for large scale technologies of D-erythro-sphingosine 1 targeting multiple tons/year production volumes.

A biotechnology approach has also been explored EP 1767644 B1 describing microbial strains capable to convert D-ribo-phytosphingosine 2 into D-erythro-sphingosine 1 with a poor conversion rate. This approach has never been industrialized and the related specific strains and enzymes have never been described in the scientific literature.

To date, access to large volumes of D-erythro-sphingosine 1 and the derivatives thereof has not been possible by using existing isolation, biotechnology and synthetic methods.

SUMMARY OF THE INVENTION

The need for large scale production of sphingoid bases, particularly D-erythro-sphingosine 1, has become a major goal of present innovative efforts due to the commercialization opportunities of important sphingolipids and glycosphingolipids desired for beneficial alteration of cognitive functions of people via the use of both pharmaceutical and nutritional solutions. This health-related aim is also coupled with the need for the syntheses of new sphingoid base/D-erythro-sphingosine derivatives which can support easy glycosylation and phosphorylation structural modifications incorporating scalable purification methods.

Sphingoid bases, especially D-erythro-sphingosine 1, have also been considered as novel nutritional, pharmaceutical or cosmetic products. Novel large volume, low cost production methods are required for sphingoid base, especially D-erythro-sphingosine 1, manufacturing to initiate commercial activities while also achieving high purities and other quality requirements of pharmaceutical, nutrition and cosmetic industries.

Thus, there is a need to have sphingolipids and their sphingoid bases, especially D-erythro-sphingosine 1, as well as their ceramides based on these compounds, available in commercially interesting amounts.

(1) The present invention provides an economically feasible process for the production Method for producing a sphingoid base of General Formula I, or a salt thereof,

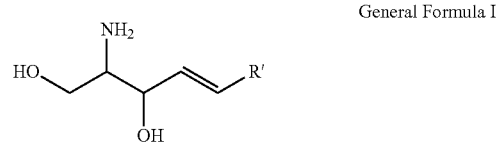

General Formula I in which R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, starting from a compound of General Formula II

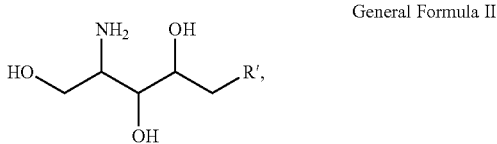

General Formula II wherein R' is as defined for General Formula I,
this method comprising the steps of:
a. protecting the amino ($NH_2$) group of a compound represented by General Formula II or a salt thereof with an N-protecting group, the N-protecting group being a vinylogous amide-type N-protecting group suitable to yield vinylogous amides,
b. protecting the hydroxyl (OH) groups at position C-1 and C-3 with an O-protecting group,
c. introducing a leaving group $R_6$ at position C-4 by substitution or replacement of the C-4 hydroxyl group,
d. inducing an elimination reaction by base treatment to form a double bond between C-4 and C-5,
e. removing the O-protecting group,
f. removing the N-protecting group.

(2) Compound of General Formula III especially obtainable by step (a) of the method of (1):

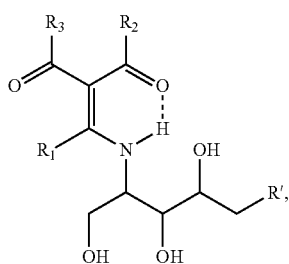

General Formula III wherein
R' is as defined in (1),
R$_1$ is selected from H, alkyl, substituted alkyl, aryl, substituted aryl,
R$_2$ and R$_3$ are independently selected from alkyl, aryl, substituted alkyl, substituted aryl, O-alkyl, substituted O-alkyl, O-aryl, substituted O-aryl, NH$_2$, NHR'', NR''R''', wherein R'' and R''' are independently selected from the group consisting of alkyl and substituted alkyl, or might form a cyclic structure characterized by 5-8 ring sizes, and
the dashed line ----- represents a hydrogen bond.

(3) Compound of General Formula IV especially obtainable by steps (a) to (b) of the method of (1):

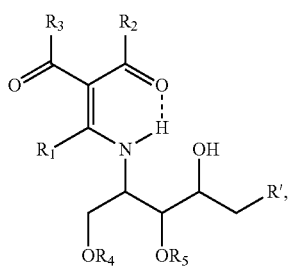

General Formula IV wherein
R', R$_1$, R$_2$ and R$_3$ are as defined in (1) or (2),
R$_4$ and R$_5$ are independently selected from optionally substituted benzyl, optionally substituted alkoxymethyl, trialkylsilyl, trialylsilyl or wherein R$_4$ and R$_5$ form a cyclic structure,
and
the dashed line ----- represents a hydrogen bond.

(4) Compound of General Formula V especially obtainable by steps (a) to (c) of the method of (1):

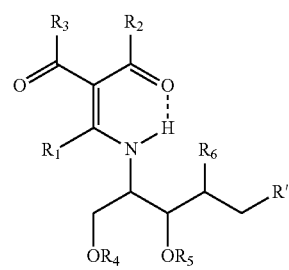

General Formula V wherein
R', R$_1$, R$_2$, R$_3$, R$_4$ and R$_5$ are as defined in (1), (2) or (3),
R$_6$ is a halide or a sulfonic ester derivative,
and
the dashed line ----- represents a hydrogen bond.

(5) Compound of General Formula V according to (4), wherein R$_6$ is a halide selected from I, Br, Cl and Br.

(6) Compound of General Formula V according to (4), wherein R$_6$ is a sulfonic ester derivative selected from mesylate (OMs), tosylate (OTs), triflate (OTf), nosylate (ONs), imidazole-1-sulfonate (OSO$_2$Im) and chlorophosphite ester (OPCl$_2$).

(7) Compound of General Formula VI especially obtainable by steps (a) to (d) of the method of (1):

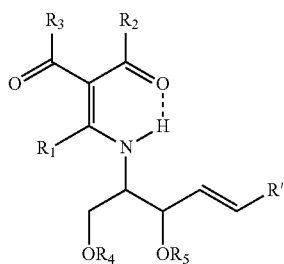

General Formula VI wherein
R', R$_1$, R$_2$, R$_3$, R$_4$ and R$_5$ are as defined in (1), (2) or (3),
and
the dashed line ----- represents a hydrogen bond.

(8) Compound of General Formula VII especially obtainable by steps (a) to (e) of the method of (1):

General Formula VII wherein
R', R$_1$, R$_2$ and R$_3$ are as defined in (1) or (2),
and
the dashed line ----- represents a hydrogen bond.

(9) Compound according to any one of (2) to (8) or method according to claim 1, wherein the stereochemical configuration of the General Formulae equals the stereochemical configuration of D-erythro-sphingosine (2S,3R,4E) and of D-ribo-phytosphingosine (2S,3S, 4R), respectively.

(10) Method according to (1), wherein the vinylogous amide-type N-protecting group is DTPM.

(11) Method according to (1), wherein the O-protecting group is an optionally substituted cyclic acetal or optionally substituted cyclic ketal.

(12) Method according to (1), wherein the O-protecting group is optionally substituted benzylidene or optionally substituted isopropylidene.

(13) Use of a sphingoid base of General Formula I obtainable by the method according to (1) for cosmetic, nutritional and/or pharmaceutical applications.

(14) Use of a compound of any one of General Formulae III to VII for the production of sphingolipids, preferably of glycosphingolipids.

The vinylogous amide N-protection strategy according to the method of the present invention enables easy introduction and easy removal of the N-protecting group and prevention of deprotonation of N—H functionality in the basic conditions of the coming elimination step that enables the formation of the $C_4$-O5 double bond. Moreover, the intermediate compounds according to General Formulae III-VII can be crystallized and have outstanding stabilities even in drastic conditions and have robust stabilities in the presence of secondary and tertiary organic bases.

DETAILED DESCRIPTION

Due to the commercial potentials of glycosphingolipids, a major aim of the present invention is to identify the most efficient syntheses of sphingoid bases, especially D-erythro-sphingosine 1, and derivatives thereof, suitable for glycosylation reactions.

Choosing the proper N-protection of sphingoid bases, especially of sphingosine and sphingosine intermediates, is a key synthetic issue of the present invention by providing chemo-, regio- and stereo-selectivities for chemical transformations.

In the present invention, the used specifications are related to molecular/technology features which have been given definitions that should be taken into consideration with the claims and the following detailed description.

The term "optionally substituted" refers to a chemical group that may either carry a substituent or may be unsubstituted.

The term "substituted" means that the group in question is substituted with a group which typically modifies the general chemical characteristics of the group in question. Preferred substituents include but are not limited to halogen, nitro, amino, azido, oxo, hydroxyl, thiol, carboxy, carboxy ester, carboxamide, alkylamino, alkyldithio, alkylthio, alkoxy, acylamido, acyloxy, or acylthio, each of 1 to 6 carbon atoms, preferably of 1 to 3 carbon atoms. The substituents can be used to modify characteristics of the molecule as a whole such as molecule stability, molecule solubility and an ability of the molecule to form crystals. The person skilled in the art will be aware of other suitable substituents of a similar size and charge characteristics, which could be used as alternatives in a given situation.

In connection with the term "alkyl", the term "optionally substituted" (or "substituted") means that the group in question may be (is) substituted one or several times, preferably 1 to 3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo, $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, l-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$ alkyl sulphinyl, $C_{1-6}$-alkylsulphonyloxy, nitro, $C_{1-6}$-alkylthio, halogen, where any alkyl, alkoxy, and the like representing substituents may be substituted with hydroxy, $C_{1-6}$ alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidino.

The term "leaving group" means a group capable of being displaced by a nucleophile in a substitution chemical reaction or can promote elimination reaction. Common leaving groups include halides, triflates (OTf), diazonium salts ($N_2$+), mesylates (OMs), tosylates (OTs), nosylates (ONs), imidazole-1-sulfonate ($OSO_2$Im) and other sulfonic esters.

The term "derivative" refers to a modified form of a compound, having one or more substituents. Especially, the terms "sphingoid base derivative", "sphingosine derivative", and "phytosphingosine derivative" include, but not limited to forms of a sphingoid base, of sphingosine, and of phytosphingosine, respectively, that have been modified to contain an N- and/or an O-protecting group on an amino-alcohol molecular scaffold, wherein the N-protecting group is a vinylogous amide-type protecting group. General Formulae III-VII, IIIa-VIIa, IIIb-VIIb and IIIc-VIIc represent derivatives of a sphingoid base. General Formulae of IIIa-IVa and IIIc-IVc, wherein $R'=C_{13}H_{27}$, represent derivatives of phytosphingosine; General Formulae VIa-VIIa and VIc-VIIc, wherein $R'=C_{13}H_{27}$, represent derivatives of sphingosine.

In the present invention, the terms "sphingosine", "D-erythro-sphingosine" and "human sphingosine" are used interchangeably. The term "human sphingosine" refers to the fact that D-erythro-sphingosine is a prevalent sphingoid base present in humans.

In the present invention, the terms "phytosphingosine" and "D-ribo-phytosphingosine" are used interchangeably.

The expression "cyclic structures characterized by 5-8 ring sizes" refers to a 5-8-membered ring, which contain single bonds and/or double bonds, which may be aromatic or not aromatic, homoaromatic or heteroaromatic, which may contain carbon atoms in the ring structure or wherein one or more of the carbon atoms may optionally be substituted or replaced by an oxygen atom, a nitrogen atom or a sulfur atom.

The expression "human identical sphingolipids" refers to sphingolipids that are naturally present in humans. Sphingolipids that are naturally present in humans contain sphingoid bases selected from D-erythro-sphingosine, D-ribo-phytosphingosine, DL-erythro-Dihydrosphingosine and 6-Hydroxy-D-erythro-sphingosine. While the carbon chains of the fatty acyl moieties in human sphingolipids usually have an even number, the carbon chains of the fatty acyl moieties in other mammals may also have odd numbers. Accordingly, "human identical sphingolipids" especially refers to sphingolipids having sphingoid bases typically present in humans and having an even number of carbon chains of their fatty acyl moieties.

The term "a" grammatically is a singular, but it may as well mean the plural of e.g. the intended compound. For example, a skilled person would understand that in the expression "the production of a sphingoid base", the production of not only one single sphingoid base, but of many sphingoid bases of the same type are meant.

In a first aspect, the present invention relates to a method for producing a sphingoid base according to General Formula I, or a salt thereof,

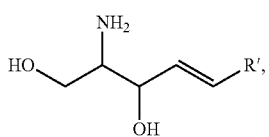
General Formula I in which R' is H, aryl or an alkyl chain having 1-43 carbon atoms, preferably 5-25 carbon atoms, more preferably 10-20 carbon atoms, which may be a straight chain or branched, and/or which may be saturated or contain one or more double bonds, and/or which may contain one or more functional groups, the functional group being preferably selected from the group consisting of a hydroxyl group, an alkoxy group, a primary, secondary or tertiary amine, a thiol group, a thioether or a phosphorus containing functional group, starting from a compound according to General Formula II

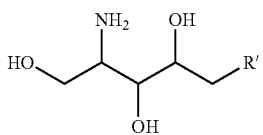
General Formula II wherein R' is as described above, this method comprising the steps of:
  a. protecting the amino ($NH_2$) group of a compound represented by General Formula II or a salt thereof with an N-protecting group, wherein the N-protecting group is a vinylogous amide-type protecting group suitable to yield vinylogous amides, to form a compound according to General Formula III:

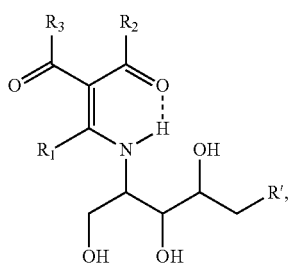
General Formula III wherein
  R' is as defined above,
  $R_1$ is selected from H, alkyl, substituted alkyl, aryl, substituted aryl,
  $R_2$ and $R_3$ are independently selected from alkyl, aryl, substituted alkyl, substituted aryl, O-alkyl, substituted O-alkyl, O-aryl, substituted O-aryl, $NH_2$, NHR'', NR''R''', wherein R'' and R''' are independently selected from the group consisting of alkyl and substituted alkyl, or might form a cyclic structure characterized by 5-8 ring sizes, and
  the dashed line ----- represents a hydrogen bond,
  b. protecting the hydroxyl (OH) groups at C-1 and C-3 of a compound of General Formula III with an O-protecting group by addition of an O-protecting group reagent to form a compound according to General Formula IV:

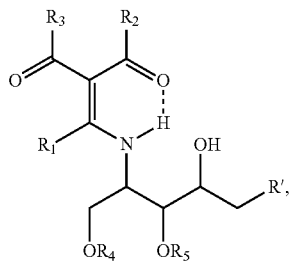
General Formula IV wherein
  R', $R_1$, $R_2$ and $R_3$ are as defined above,
  $R_4$ and $R_5$ are independently selected from optionally substituted benzyl, optionally substituted alkoxymethyl, trialkylsilyl, trialylsilyl or wherein $R_4$ and $R_5$ form a cyclic structure,
and
  the dashed line ----- represents a hydrogen bond,
  c. introducing a leaving group $R_6$ at C-4 position of a compound of General Formula IV, by substitution or replacement of the C-4 hydroxyl group to form a compound according to General Formula V:

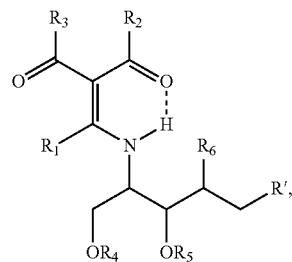
General Formula V wherein
  R', $R_1$, $R_2$, $R_3$, $R_4$ and $R_5$ are as defined above,
  $R_6$ is a halide, such as I, Br, Cl or F, or a sulfonic ester derivative, such as mesylate (OMs), tosylate (OTs), triflate (OTf), nosylate (ONs), imidazole-1-sulfonate ($OSO_2Im$) or chlorophosphite ester ($OPCl_2$),
and
  the dashed line ----- represents a hydrogen bond,
  d. inducing an elimination reaction in a compound of General Formula V by base treatment to form a double bond between the C-4 and C-5 carbon atoms, resulting in a compound according to General Formula VI

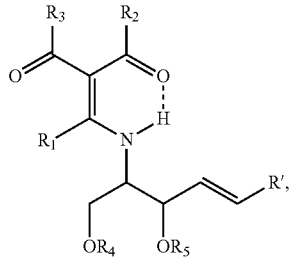
General Formula VI wherein

R', $R_1$, $R_2$, $R_3$, $R_4$ and $R_5$ are as defined above, and the dashed line ----- represents a hydrogen bond, e. removing the O-protecting group of a compound of General Formula VI to form a compound according to General Formula VII

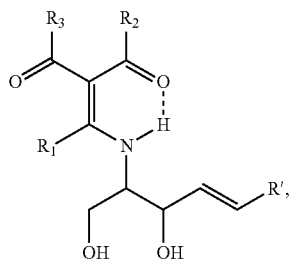

General Formula VII wherein

R', $R_1$, $R_2$ and $R_3$ are as defined above, and the dashed line ----- represents a hydrogen bond, f. removing the N-protecting group of a compound of General Formula VII, to form a sphingoid base according to General Formula I, or a salt thereof.

Accordingly, the present invention provides a method for the production of a sphingoid base according to General Formula I or a salt thereof, starting from a compound according to General Formula II or a salt thereof, and having compounds according to General Formulae III-VII as intermediate compounds. The method of the present invention is preferably a synthetic method.

The skilled person will be aware that position C-1, C-2, C-3, C-4 and $C_5$ refer to the carbon atoms of the sphingoid base of General Formula II, even if substituents would strictly taken change the exact positions of the carbon atoms. In other words, when speaking of C-1, C-2, C-3, C-4 and $C_5$, reference is herein always made to the respective carbon atoms of the sphingoid base of General Formula II.

The salts of the compounds of General Formula I and General Formula II are preferably pharmaceutically acceptable salts or other generally acceptable salts, unless they would be excluded for chemical reasons, which the skilled person will readily understand.

In a preferred embodiment, the stereochemistry of a compound according to General Formula I and II, or of salts thereof, and accordingly of an intermediate compound according to General Formula III-VII, corresponds to the stereochemistry of D-erythro-sphingosine and of D-ribo-phytosphingosine, respectively. In other words, the stereochemical configuration of the compounds of General Formulae I to VII preferably equals the stereochemical configuration of D-erythro-sphingosine (2S,3R,4E) and of D-ribo-phytosphingosine (2S,3S,4R), respectively. More precisely, the stereochemical configuration of the compounds of General Formulae II to V is (2S,3S,4R) and the stereochemical configuration of the compounds of General Formulae I, VI and VII is (2S,3R,4E). Those preferred compounds are represented by General Formulae IIIa to VIIa.

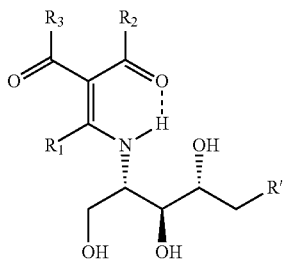

General Formula IIIa

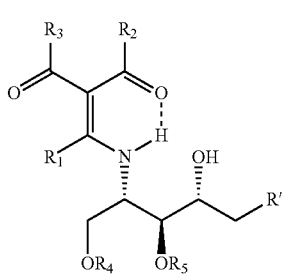

General Formula IVa

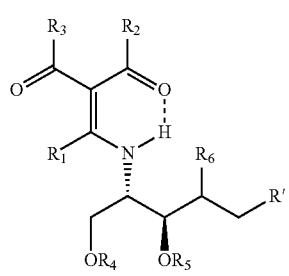

General Formula Va

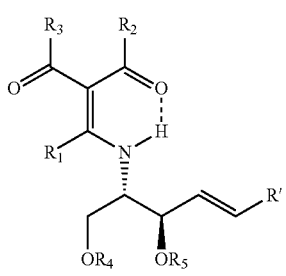

General Formula VIa

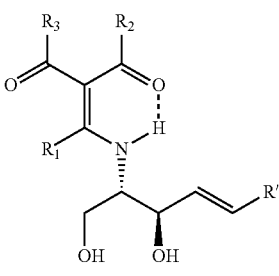

General Formula VIIa wherein

R', $R_1$, $R_2$, $R_3$, $R_4$, $R_5$ and $R_6$ are as defined above, and the dashed line ----- represents a hydrogen bond.

In a more preferred embodiment, R' of General Formulae I to VII or of General Formulae Ia to VIIa is an alkyl chain having 13 carbon atoms. Even more preferably, R' of General Formula I to VII is $C_{13}H_{27}$ or $CH(OH)C_{12}H_{25}$, especially —$C_{13}H_{27}$ or —$CH(OH)C_{12}H_{25}$.

The skilled person will understand that the starting compound of General Formula II defines the possible General Formulae of the following steps of the method of the present invention. If e.g. a compound of General Formula Ia is used as a starting compound for the method, a compound of General Formula IIIa (and not a compound of General Formula IIIb) may be formed in step (a) of the method of the present invention.

In step (a) of the method of the present invention, the $NH_2$ (amino) group of a compound represented by General Formula II, preferably of phytosphingosine 2, is protected with an N-protecting group by addition of an N-protecting group reagent being a vinylogous reagent to form a compound according to General Formula III, preferably General Formula IIIa.

The vinylogous reagent may be a vinylogous acid, a vinylogous ester, a vinylogous amide or a vinylogous acid halide. Preferably, the vinylogous reagent is an N,N-disubstituted vinylogous amide reagent, more preferably an N,N-dialkyl-barbituric acid-derived reagent. Even more preferably, the vinylogous reagent is 1,3-dimethyl-5-[(dimethylamino)methylene]-2,4,6(1H,3H,5H)-trioxopyrimidine (DTPM-reagent) (CAS: 35824-98-7; $C_9H_{13}N_3O_3$).

When DTPM-reagent is used as the vinylogous reagent, a compound of General Formula IIIb or preferably of General Formula IIIc is formed.

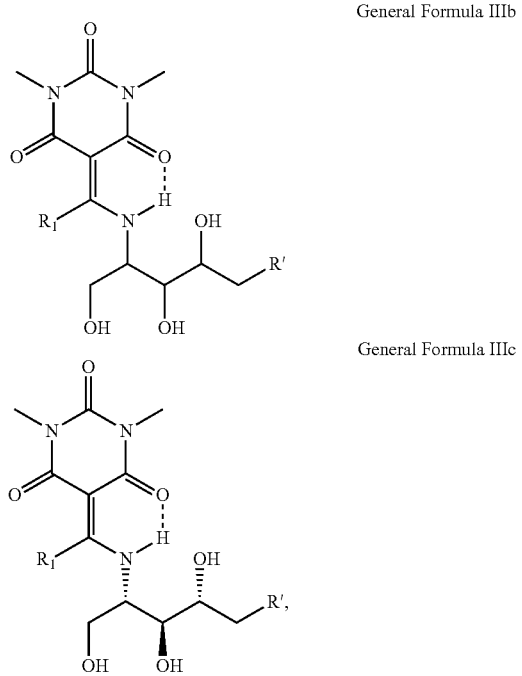

General Formula IIIb

General Formula IIIc wherein
R' and $R_1$ are as defined above,
and
the dashed line ----- represents a hydrogen bond.

The vinylogous reagent preferably has a cyclic structure providing a robust stability and crystalline properties. The preparation of vinylogous reagents are described in publications *Tetrahedron Letters,* 2001, 42, 3129-3132; WO 98/38197. For the preparation, the compound according to General Formula II and the vinylogous reagent may be mixed in water, organic solvents or in their aqueous mixtures. The reactions may optionally be catalyzed with organic or inorganic bases at temperatures ranges from 0-150° C., preferably at temperatures ranging from 20-120° C. More preferably, the reaction goes to completion at ambient temperature. The reactions are preferably carried out in organic solvents at room temperature (r.t.) or between 40-100° C. A person skilled in art has the knowledge to conduct, isolate and purify the novel compounds by using standard methods of synthetic organic chemistry.

DTPM protection of carbohydrates and primary amines are well documented and their preparation are known for the person skilled in Art (*Tetrahedron Letters,* 2001, 42, 3129-3132).

Preferably, the introduction of DTPM protecting group may be performed using the DTPM-reagent dissolved in $H_2O$ or in organic solvents, such as methanol and $CH_2Cl_2$. The reaction does not require extreme conditions and affords high conversion. The DTPM-protected compounds of General Formula IIIb and IIIc may be precipitated directly from the reaction mixtures.

Example 1 (see below under "Examples") provides a representative experimental example of the described DTPM-protection.

In step (b) of the method of the present invention, the hydroxyl groups at C-1 and C-3 of a compound of General Formula III, preferably of General Formula IIIa or General Formula IIIb, more preferably of General Formula IIIc, are protected with an O-protecting group by addition of an O-protecting group reagent.

The O-protecting groups at C-1 and C-3 may be the same or different and are selected from optionally substituted benzyl, optionally substituted alkoxymethyl, trialkylsilyl, trialylsilyl or preferably one O-protecting group may form one cyclic structure with the hydroxyl groups of both C-1 and C-3. More preferably, the O-protecting group forming the cyclic structure with the hydroxyl groups of both C-1 and C-3 is an optionally substituted cyclic carbonate, an optionally substituted cyclic acetal or an optionally substituted cyclic ketal, even more preferably an optionally substituted cyclic acetal or an optionally substituted cyclic ketal. Especially, the optionally substituted cyclic acetal is an optionally substituted benzylidene and the optionally substituted cyclic ketal is an optionally substituted isopropylidene.

The introduction of an O-protecting group used is a well-known process for a person skilled in art by reacting 1,3-diols of compounds characterized by General Formula III, IIIa, IIIb or IIIc with aldehyde, ketone, acyclic dialkylacetals or acyclic dialkylketal, preferably dimethyl acetal and dimethyl ketal, reagents in the presence of protic acid or Lewis acid catalysts in organic solvents.

The acetal or ketal formation is catalyzed by acid catalysts such as strong organic or inorganic acids, including protic acids such as tosic acid, camphorsulfonic acid, acidic ion-exchange resin, HCl, $H_2SO_4$, etc.

Example 2 (see below under "Examples") provides one representative experimental example for step (b) of the method of the present invention.

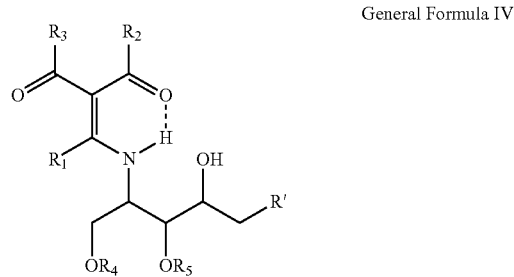

General Formula IV

-continued

General Formula IVa

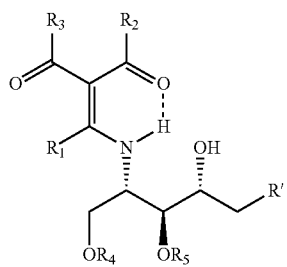

General Formula IVb

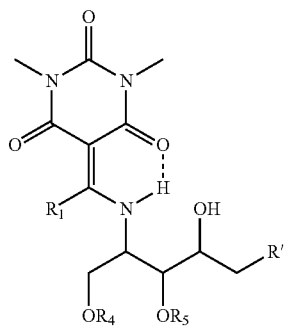

General Formula IVc

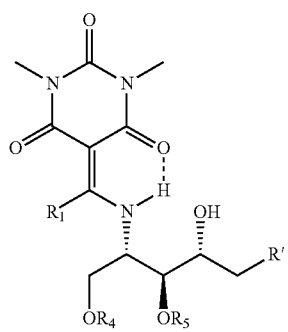

wherein

R', $R_1$, $R_2$, $R_1$, $R_4$ and $R_5$ are as defined above, and the dashed line ----- represents a hydrogen bond.

When the O-protecting group forming the cyclic structure with the hydroxyl groups of both C-1 and C-3 is an optionally substituted cyclic acetal or an optionally substituted cyclic ketal, a compound according to General Formula IV' is formed. The preferred embodiments shown in General Formulae IIIa, IIIb and IIIc apply equally to a compound according to General Formula IV'.

General Formula III'

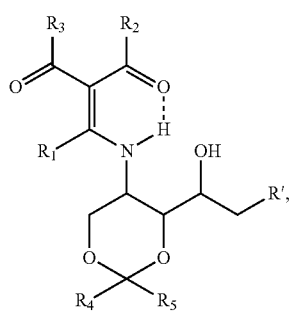

wherein

R', $R_1$, $R_2$ and $R_3$ are as defined above, $R_4$ and $R_5$ form an optionally substituted cyclic acetal or an optionally substituted cyclic ketal, and the dashed line ----- represents a hydrogen bond.

In step (c) of the method of the present invention, a leaving group $R_6$ is introduced at C-4 position of General Formula IV, preferably of General Formula IVa or of General Formula IVb, more preferably of General Formula IVc, by substitution or replacement of the C-4 hydroxyl group, to form a compound according to General Formula V, preferably General Formula Va or General Formula Vb, more preferably General Formula Vc, respectively.

$R_6$ may be a halide, such as I, Br, Cl or F, or a sulfonic ester derivative such as mesylate (OMs), tosylate (OTs), triflate (OTf), nosylate (ONs), imidazole-1-sulfonate ($OSO_2Im$) and chlorophosphite ester ($OPCl_2$).

When $R_6$ is a halide, it may preferably be introduced by using triphenylphosphine ($PPh_3$), imidazole and iodine or bromine, preferably iodine.

When $R_6$ is a sulfonic ester, the respective sulfonic acid chlorides or anhydrides may be employed in the presence of a base, preferably in the presence of an organic base, more preferably in the presence of pyridine, triethylamine (TEA) or diisopropylethylamine (DIPEA) for the introduction of the sulfonic ester moiety.

Step (c) requires neutral or basic conditions to keep the acetal or ketal protection group at C-1 and C-3 position of the compound stable. Thus, mesylation, tosylation, imidazoylsulfonylation can use simple organic bases like pyridine, triethylamine along with the required reagents of mesylchloride, tosylchloride, etc. on organic solvents like dichloromethane, toluene, etc. Deoxy iodination usually takes place in dichloromethane in the presence of triphenylphosphine/$I_2$/imidazole reagent combinations known by the person skilled in Art. Chlorophosphate esterification preferably requires pyridine/$POCl_3$ reagent pair acting in dichloromethane, toluene or pyridine.

Example 3 (see below under "Examples") provides one representative representative example for step (c) of the method of the present invention.

General Formula V

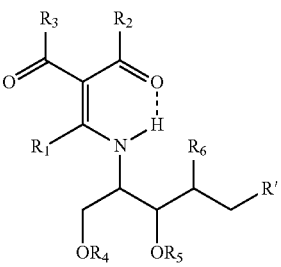

General Formula Va

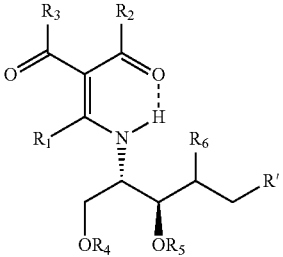

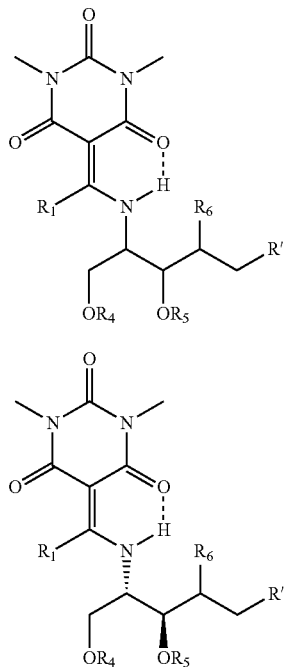

General Formula Vb

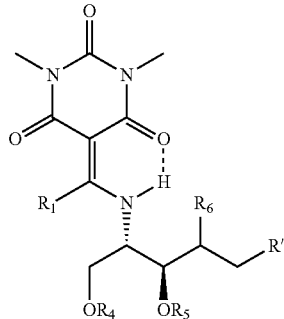

General Formula Vc

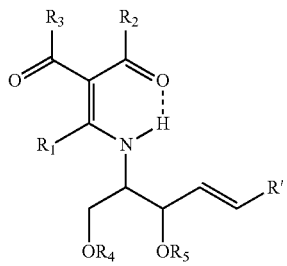

General Formula VI

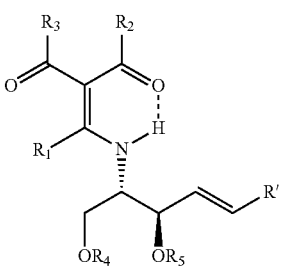

General Formula VIa

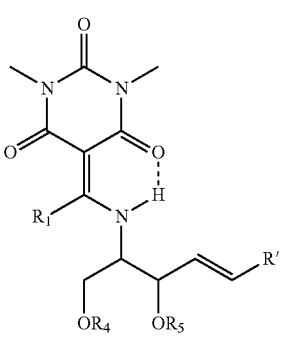

General Formula VIb

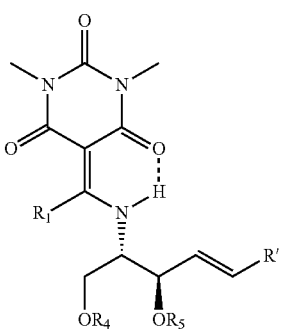

General Formula VIc wherein

R', $R_1$, $R_2$, $R_1$, $R_4$, $R_5$ and $R_6$ are as defined above, and the dashed line ----- represents a hydrogen bond.

In step (d) of the method of the present invention, an elimination reaction is induced to form a double bond between the C-4 and C-5 carbon atoms of a compound according to General Formula V, preferably General Formula Va or General Formula Vb, more preferably General Formula Vc, resulting in a compound according to General Formula VI, preferably General Formula VIa or General Formula VIb, more preferably General Formula VIc, respectively.

Elimination reactions are often accompanied by nucleophilic substitution reactions as competing reactions. However, conditions could be found in the present invention to make the elimination reaction the main, dominant reaction; for example, strong bases and weak nucleophiles favor the elimination products and are therefore preferred.

In a preferred embodiment of the present invention, bulky, sterically hindered non-nucleophilic bases such as KOtBu, DBU or DBN are used to promote the elimination reaction. The elimination reaction appears to take place with virtually complete selectivity towards the desired trans-sphingoid base, which appeared to be virtually free of unwanted side products.

Preferably, organic solvents such as acetonitrile, 2-methyltetrahydrofuran, propionitrile, 1,4-dioxane, toluene, xylene or N,N-dimethylformamide may be used to perform the elimination reaction. The elimination reaction is preferably performed at a temperature range between 60 to 150° C.

Example 4 (see below under "Examples") provides one representative experimental example for step (d) of the method of the present invention.

wherein

R', $R_1$, $R_2$, $R_1$, $R_4$, and $R_5$ are as defined above, and the dashed line ----- represents a hydrogen bond.

In step (e) of the method of the present invention, the O-protecting group(s) is/are removed from a compound of General Formula VI, preferably from a compound according to General Formula VIa or General Formula VIb, more preferably from a compound according to General Formula VIc, to form a compound according to General Formula VIIa or General Formula VIIb, more preferably from a compound according to General Formula VIIc, respectively.

The O-protecting group(s) may be removed via deprotecting procedures carried out in acidic conditions. A typical example demonstrates the removal of 1,3-acetal or ketal groups in acidic conditions in the presence of water or alcohols catalyzed by inorganic or organic acid catalysts such as HCl, TsOH, camphorsulfonic acid, acidic ion exchange resin, etc. at temperatures ranging from 0-130° C. Vinylogous amides are stable in such conditions.

Example 5 (see below under "Examples") provides one representative experimental example for step (e) of the method of the present invention.

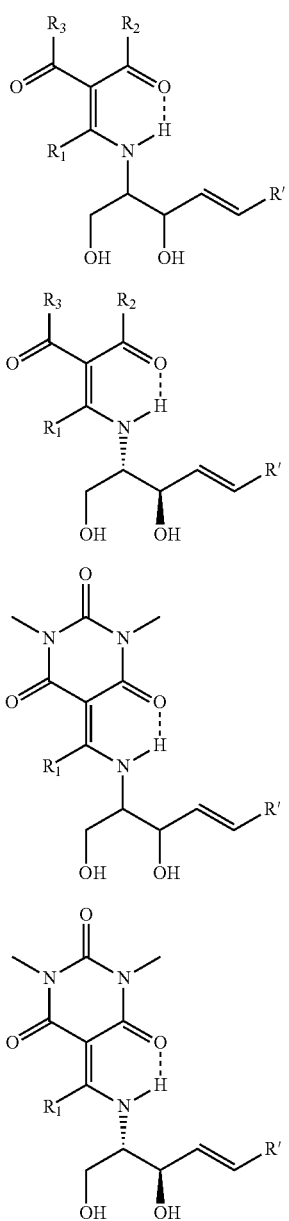

General Formula VII

General Formula VIIa

General Formula VIIb

General Formula VIIc

In step (f) of the method of the present invention, the N-protecting group is removed from a compound of General Formula VII, preferably from a compound according to General Formula VIIa or from a compound according to General Formula VIIb, more preferably from a compound according to General Formula VIIc, to form a compound according to General Formula I, preferably D-erythro-sphingosine 1, or a salt thereof.

The reagent used for this step may be selected from an aqueous inorganic base, $NH_3$, primary amines, hydrazine, hydrazine derivatives, hydroxylamine and hydroxylamine derivatives. The reaction may be performed in an organic solvent such as dichlormethane, acetonitrile, methanol, tetrahydrofuran or toluene. The preferred temperature range for the reaction is from 20 to 120° C.

Example 7 (see below under "Examples") provides a representative experimental example for step (f) of the method of the present invention.

Steps (a) to (f) of the method of the present invention are performed in the order mentioned, i.e. beginning with step (a), continuing with step (b), (c), (d), (e) and ending with step (f). In an alternative embodiment, however, steps (e) and (f) of the method of the present invention may be swapped. That means that the removal of the N-protecting group may be performed before the removal of the O-protecting group. Example 7 (see below under "Examples") provides a representative experimental example for this alternative embodiment, wherein step (f) is performed on a compound still carrying the O-protecting group, i.e. wherein step (e) has not been performed yet.

The method of the present invention may as well comprise further steps in addition to steps (a) to (f), provided they do not negatively affect the reactions of steps (a) to (f), which the skilled person will easily determine.

In a second aspect, the present invention provides novel intermediate compounds of the method according to the present invention, represented by General Formulae III to VII.

The General Formulae of the (preferred) intermediate compounds are not illustrated again. A skilled person will be aware, however, that the General Formulae and the defined rests (R) as defined above in detail will also apply to the intermediate compounds.

Preferably, the intermediate compounds are represented by General Formulae IIIa to VIIa or by General Formulae IIIb to VIIb. More preferably, the intermediate compounds are represented by General Formulae IIIc to VIIc.

In a preferred embodiment, R' of General Formulae III to VII (or the preferred versions of General Formulae IIIa to VIIa, IIIb to VIIb or IIIc to VIIc) is an alkyl chain having 13 carbon atoms. Even more preferably, R' of General Formulae III to VII (or the preferred versions of General Formulae IIIa to VIIa, IIIb to VIIb or IIIc to VIIc) is $C_{13}H_{27}$ or $CH(OH)C_{12}H_{25}$, especially —$C_{13}H_{27}$ or —$CH(OH)C_{12}H_{25}$.

A compound represented by General Formula III, IIIa, IIIb or IIIc is especially obtained by step (a) of the method of the present invention.

A compound represented by General Formula IV, IVa, IVb or IVc is especially obtained by steps (a) to (b) of the method of the present invention.

A compound represented by General Formula V, Va, Vb or Vc is especially obtained by steps (a) to (c) of the method of the present invention.

A compound represented by General Formula VI, VIa, VIb or VIc is especially obtained by steps (a) to (d) of the method of the present invention.

A compound represented by General Formula VII, VIIa, VIIb or VIIc is especially obtained by steps (a) to (e) of the method of the present invention.

A compound of General Formulae III to VII, preferably of General Formulae IIIa to VIIa or of General Formulae IIIb to VIIb, more preferably of General Formulae IIIc to VIIc VII, VIa, VIIb or VIIc is suitable for glycosylation, phosphorylation and other nucleophilic O-substitution reactions—due to its enhanced O-nucleophilicity. Accordingly, a compound of General Formulae III to VII, preferably of General Formulae IIIa to VIIa or of General Formulae IIIb to VIIb, more preferably of General Formulae IIIc to VIIc VII, may be used for the preparation of sphingolipids such as glycosphingolipids, glycosylsphingosines, sphingosine-1-O-phosphates, sphingomyelins, phosphosphingolipids, or glycosylinositol phosphoceramides; especially, a compound of General Formulae III to VII, preferably of General Formulae IIIa to VIIa or of General Formulae IIIb to VIIb, more preferably of General Formulae IIIc to VIIc, may be used for the preparation of glycosphingolipids. The most preferred compound for such use is a compound of General Formula VII, preferably of General Formula VIIa or of General Formula VIIb, more preferably of General Formula VIIc.

In the present context, sphingolipids are optionally substituted compounds containing a sphingoid base characterized by the presence of a molecular motif of General Formula I or II. Preferred substituents are carbohydrate- and/or phosphate-containing moieties of naturally occurring sphingolipids.

A compound of General Formula I obtainable by the method according to the present invention may be used for cosmetic, nutritional and/or pharmaceutical applications.

In one embodiment, a compound of General Formula I obtainable by the method according to the present invention may be used as a pharmaceutical agent and/or for the preparation of a pharmaceutical composition.

In another embodiment, a compound of General Formula I obtainable by the method according to the present invention may be used for the preparation of a nutritional formulation, e.g. a food supplement.

In yet another embodiment, a compound of General Formula I obtainable by the method according to the present invention may be used for the preparation of a cosmetic product.

A compound of General Formula I, preferably of General Formula Ia, obtainable by the method according to the present invention, may also be used for the production of ceramides, phosphosphingolipids or glycosphingolipids.

The production of ceramides, phosphosphingolipids or glycosphingolipids may be performed by N-acylation. N-acylation may be performed using an acyl moiety of a $C_{12}$-$C_{30}$ acyl group which can be saturated, unsaturated or optionally substituted. The acylation may be performed by both lipase-assisted biocatalysis or chemistry via the use of the corresponding carboxylic acid, acid chloride, ester or anhydride in the presence of a base, preferably in the presence of an organic base, more preferably in the presence of pyridine, triethylamine (TEA) or diisopropylethylamine (DIPEA).

Other features of the invention will become apparent in the course of the following descriptions of exemplary embodiments which are given for illustration of the invention and are not to be limiting thereof.

EXAMPLES

Analytical Methods
General Methods and Materials $^1$H NMR and $^{13}$C NMR was recorded with a Bruker WM-300S (300/75.1 MHz) spectrometer. $^1$H and $^{13}$C chemical shifts are given in ppm (δ) relative to tetramethylsilane (δ=0.00), CDCl$_3$ (δ=77.00) as internal standard. TLC-analysis was performed with silica gel TLC-plates (Merck, Silica gel, F254) with detection by UV-absorption (254 nm) where applicable and carring (±140° C.) with ammonium molybdate (25 g/L) and cerium ammonium sulfate (10 g/L) in 10% H2SO4. Column chromatography was performed on Silica gel 60 (220-440 mesh ASTM, Fluka).

Preparation of 1,3-dimethyl-5-[(dimethylamino)methylene]-2,4,6(1H,3H,5H)-trioxopyrimidine (DTPM reagent N,N-dimethylformamide dimethyl acetal (252 g, 2.11 mol) was stirred at 0° C. in CH$_2$Cl$_2$ (750 mL). 1,3-Dimethylbarbituric acid (300 g, 1.92 mol) in CH$_2$Cl$_2$ (2 L) was added to the stirring solution over 2 hours. The reaction mixture was washed with water (3×1 L) and saturated brine solution (1 L). The organic phase was dried over MgSO$_4$, filtered and evaporated to dryness under vacuum. The residue was re-suspended in diethyl ether (750 mL), filtered and washed on the funnel with additional diethyl ether (500 mL) to yield 1,3-dimethyl-5-[(dimethylamino)methylene]-2,4,6 (1H,3H,5H)-trioxopyrimidine as a yellow solid (271.85 g, 67%).

Example 1

Preparation of (2S,3S,4R)-24(1,3-dimethyl-2,4,6 (1H,3H,5H)-trioxopyrimidine-5-ylidene)methyl)-octadecan-1,3,4-triol D-ribo-Phytosphingosine (4.8 g, 15.1 mmol) is added to methanol (150 mL) at room temperature (r.t.). and heated to approx. 30° C. until complete dissolution of the solid. The solution is cooled to r.t., then DTPM-reagent (3.5 g, 16.6 mmol) is added in one portion, and the stirring is continued at r.t. for 1 h. (After approx. 5 min. crystallization of the product starts.) The slurry is cooled to approx. 5° C., then kept at 5° C. for 2 h. The solid is filtered off (easy filtration on G3), washed with cold methanol (20 mL, 5° C.), then dried in a vacuum oven (30 mbar/40° C./12 h). Yield: 6.06 g (83%).

$^1$H NMR (DMSO): 10.4 (dd, 1H), 8.15 (d, 1H), 5.30 (d, 1H), 4.85 (m, 1H), 4.68 (d, 1H), 3.75 (m, 2H), 3.51 (m, 1H), 3.41 (m, 1H), 3.27 (m, 1H), 3.15 and 3.14 (2×s, 3-3H), 1.61 (m, 1H), 1.43 (m, 1H), 1.23 (m, 24H), 0.84 (t, 3H).

$^{13}$C NMR (DMSO): 163.97, 162.17, 159.2, 151.58, 89.23, 73.71, 70.71, 64.47, 59.03, 33.69, 31.26, 29.18, 28.9, 28.67, 27.32, 26.68, 24.85, 22.06, 13.92.

Example 2

Preparation of (2S,3S,4R)-24(1,3-dimethyl-2,4,6 (1H,3H,5H)-trioxopyrimidine-5-ylidene)methyl)-1, 3-(benzylidene)-octadecan-4-ol The suspension of (2S,3S,4R)-2-NHDTPM-octadecan-1, 3,4-triol (4.1 g, 8.5 mmol) in acetonitrile (41 mL) is heated to 70° C. Benzaldehyde dimethyl acetal (1.64 mL, 10.9 mmol), then CSA (600 mg, 2.6 mmol) is added. The solid dissolves instantly. The solution is stirred at 70° C. for 2 h, then cooled to 50° C. Crystallization of the product starts in 15-20 min. The suspension is stirred at 50° C. for additional 2 h, then cooled to 5° C. After 1 h stirring at 5° C., acetonitrile (10 mL) is added (since the suspension is too thick), the solid is filtered off, washed with acetonitrile (2×10 mL, 5° C.) and dried in vacuum oven (15 mbar/45° C./12 h). Yield: 4.1 g (85%) of white solid.

$^1$H NMR (CDCl$_3$): 10.35 (dd, 1H), 8.25 (d, 1H), 7.4-7.5 (m, 5H), 5.54 (s, 1H), 4.40 (dd, 1H), 3.90 (m, 2H), 3.80

(m, 2H), 3.30 and 3.32 (2×s, 3-3H), 2.42 (m, 1H), 1.55 (m, 3H), 1.3 (m, 24H), 0.9 (t, 3H)
$^{13}$C NMR (CDCl$_3$): 165.06, 162.66, 158.85, 151.93, 136.86, 129.39, 128.39, 126.06, 101.18, 92.04, 81.65, 73.16, 69.59, 53.58, 32.94, 31.93, 29.69, 29.60, 29.56, 29.46, 29.36, 27.93, 27.18, 25.71, 22.70, 14.13

Example 3

Preparation of (2S,3S,4S)-2-((1,3-dimethyl-2,4,6 (1H,3H,5H)-trioxopyrimidine-5-ylidene)methyl)-1,3-(benzylidene)-4-iodooctadecan (2S,3S,4R)-2-NHDTPM-1,3-(benzylidene)-octadecan-4-ol (2.0 g, 3.5 mmol) is added to toluene (130 mL), and heated to 50-52° C. (The solid does not dissolve completely at r.t. On heating it goes to solution.) Triphenylphosphine (1.88 g, 7.2 mmol) and imidazole (1.24 g, 18.2 mmol) is added, and the suspension is stirred until clear solution is obtained (triphenylphosphine dissolves readily, imidazole dissolves in approx. 10-15 min.). Iodine (1.64 g, 6.5 mmol) is added, and the reaction mixture is heated to 80-82° C., and stirred for 12 h. The mixture is cooled to r.t., washed with aqueous solution of sodium thiosulfate (1×40 mL, 10%), hydrochloric acid (2×40 mL, 0.1M), then sodium chloride (2×40 mL, 10%, pH 1$^{st}$ wash~3, pH 2$^{nd}$ wash~6). The organic phase is then dried (MgSO$_4$), the solid is filtered off, and the filtrate is concentrated in vacuo to a syrup (approx. 4.3 g). The crude product is purified on a column of silica gel (150 g, eluent dichloromethane: acetone 95: 5). Yield: 2.21 g colourless foam (93%).
$^1$H NMR (CDCl$_3$): 10.12 (dd, 1H), 8.4 (d, 1H), 7.55-7.45 (m, 5H), 5.7 (s, 1H), 4.4 (dd, 1H), 4.12 (dd, 1H), 4.05 (m, 1H), 3.98 (t, 1H), 3.4 and 3.35 (2×s, 3-3H), 3.08 (dd, 1H), 2.15 (m, 1H), 1.83 (m, 1H), 1.3 (m, 24H), 0.9 (t, 3H)
$^{13}$C NMR (CDCl$_3$): 165.39, 162.35, 159.28, 151.87, 136.76, 129.44, 128.41, 126.27, 101.26, 92.75, 80.64, 69.19, 58.55, 37.23, 34.89, 31.93, 29.68, 29.53, 29.42, 28.85, 27.97, 27.23, 22.70, 14.13.

Example 4

Preparation of (2S,3R,4E)-2-((1,3-dimethyl-2,4,6 (1H,3H,5H)-trioxopyrimidine-5-ylidene)methyl)-1,3-(benzylidene)octadec-4-ene (2S,3S,4S)-2-NHDTPM-1,3-(benzylidene)-4-iodooctadecan (2.0 g, 2.9 mmol) is dissolved in toluene (150 mL). Toluene (~50 mL) is distilled off (atm. pressure, 175° C. oil bath) to remove traces of water. The solution is cooled to 120° C. under argon. DBU (1.33 mL 8.9 mmol) is added, and the reaction mixture is stirred at 120° C. for 5 h. The reaction mixture is cooled to r.t., washed with aq. solution of HCl (0.1 M, 2×50 mL, slow phase separation!), then solution of NaCl (10%, 2×50 mL, slow phase separation). The organic phase is dried (MgSO$_4$), the solid is filtered off, and the filtrate is concentrated in vacuo to a brown syrup (1.76 g). Chromatographic purification (Silica gel, 150 g, eluent hexane: ethyl-acetate 85:15) yields colourless syrup (1.21 g, 75%).
$^1$H NMR (CDCl$_3$): 10.1 (dd, 1H), 8.12 (d, 1H), 7.51-7.37 (m, 5H), 5.85 (m, 1H), 5.57 (s, 1H), 5.47 (dd, 1H), 4.42 (dd, 1H), 4.15 (t, 1H), 3.84 (t, 1H), 3.51 (m, 1H), 3.32 (2×s, 6H), 2.04 (m, 2H), 1.25 (m, 23H), 0.9 (t, 3H).
$^{13}$C NMR (CDCl$_3$):165.27, 162.62, 159.42, 152.01, 139.16, 137.04, 129.41, 128.48, 126.25, 124.62, 101.44, 91.96, 81.78, 69.56, 57.34, 32.53, 32.02, 29.8, 29.77, 29.75, 29.66, 29.59, 29.46, 29.37, 29.24, 28.98, 28.00, 27.27, 22.79, 14.23.

Example 5

Preparation of (2S,3R,4E)-2-((1,3-dimethyl-2,4,6 (1H,3H,5H)-trioxopyrimidine-5-ylidene)methyl)-4-octadecen-1,3-diol (2S,3R,4E)-2-NHDTPM-1,3-(benzylidene)-octadec-4-ene (800 mg, 1.4 mmol) is dissolved in THF (10 mL), then methanol (20 mL) and CSA (200 mg) are added. The mixture is stirred at 45° C. for 2.5 h. The mixture is cooled to r.t. On cooling, crystallization started. The slurry is stirred at r.t. for 3 h. The solid is filtered off, and washed with methanol (5 mL, r.t.), and dried in vacuum drying oven at 50° C. to yield 250 mg white solid. Pyridine (1 mL) is added to the filtrate, and filtrate is concentrated in vacuo to a yellow syrup (800 mg). This is purified on a column of silica (120×, eluent dichloromethane: acetone 85: 15, then 7: 3; The eluent dissolves the crude syrup.) to yield 250 mg of off-white solid. Overall yield: 74%.
$^1$H NMR (CDCl$_3$): 10.45 (m, 1H), 8.18 (d, 1H), 5.8 (m, 1H), 5.47 (m, 1H), 4.35 (m, 1H), 3.91 (m, 2H), 3.51 (m, 1H), 3.22 (2×s, 6H), 3.09 (t, 1H), 2.77 (d, 1H), 2.03 (m, 2H), 1.24 (m, 23H), 0.88 (t, 3H).
$^{13}$C NMR (CDCl$_3$): 164.97, 163.24, 159.7, 152.11, 136.67, 127.34, 91.05, 73.26, 66.01, 61.65, 32.47, 32.06, 29.82, 29.79, 29.73, 29.63, 29.49, 29.34, 29.16, 28.02, 27.3, 22.82, 14.25.

Example 6

Preparation of (2S,3R,4E)-2-amino-4-octadecen-1,3-diol (2S,3R,4E)-2-NHDTPM-4-octadecen-1,3-diol (500 mg, 1.07 mmol) is dissolved in methanol (5 mL), then 0.7 mL 25% ammonia solution is added. The reaction mixture is stirred at 45° C. for 3 h, then the mixture is cooled down to r.t. and stirred at r.t. for 1 h. Then the reaction mixture is concentrated in vacuo and the residue was purified by column chromatography to afford the desired product as a white solid (300 mg). Yield: 93%
$^1$H NMR (CD$_3$OD): 5.73 (m, 1H), 5.49 (dd, 1H), 3.96 (dd, 1H), 3.68 (dd, 1H), 3.49 (dd, 1H), 2.74 (m, 1H), 2.08 (m, 2H), 1.45-1.2 (m, 23H), 0.89 (t, 1H).
$^{13}$C NMR (CD$_3$OD): 135.38, 130.98, 75.3, 64.53, 58.14, 33.6, 33.23, 30.84, 30.91, 30.89, 30.78, 30.63, 30.53, 30.49, 23.89, 14.59.

Example 7

Preparation of (2S,3R,4E)-2-amino-1,3-(benzylidene)octadec-4-ene (2S,3R,4E)-2-NHDTPM-1,3-(benzylidene)octadec-4-ene (1 g, 1.8 mmol) is dissolved in THF (10 mL), then 2 mL 25% ammonia solution is added. The reaction mixture is stirred at 45° C. for 3 h, then the mixture is cooled down to r.t. and stirred at r.t. for 1 h. Then the reaction mixture is concentrated in vacuo and the residue was purified by column chromatography to afford the desired product as a white solid (550 mg). Yield: 78%

$^1$H NMR (CDCl$_3$): 7.42-7.3 (m, 5H), 5.77 (m, 1H), 5.49 (m, 1H), 5.41 (dd, 1H), 4.34 (m, 1H), 4.05 (m, 2H), 3.77 (m, 1H), 3.44 (m, 1H), 1.97 (m, 2H), 1.15 (m, 23H), 0.81 (t, 3H).

$^{13}$C NMR (CDCl$_3$): 139.07, 137.05, 129.51, 128.45, 125.98, 124.57, 101.24, 82.25, 69.8, 56.08, 31.2, 29.7, 29.68, 29.65, 29.54, 29.36, 29.2, 27.96, 27.24, 25.49, 22.69, 14.12.

The invention claimed is:

1. A method for producing a sphingoid base of Formula I, or a salt thereof,

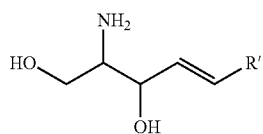

Formula I in which R' is H, aryl or an alkyl chain having 1-43 carbon atoms, which may be a straight chain or branched, and/or which may be saturated or contain one or more double bonds, and/or which may contain one or more functional groups, the functional group being selected from the group consisting of a hydroxyl group, an alkoxy group, a primary, secondary or tertiary amine, a thiol group, a thioether and a phosphorus containing functional group, starting from a compound of Formula II

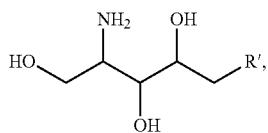

Formula II wherein R' is as defined for Formula I, this method comprising the steps of:

a. protecting the amino (NH$_2$) group of a compound represented by Formula II or a salt thereof with an N-protecting group, the N-protecting group being a vinylogous amide-type N-protecting group suitable to yield vinylogous amides, b. protecting the hydroxyl (OH) groups at position C-1 and C-3 with an O-protecting group, c. introducing a leaving group R$_6$ at position C-4 by substitution or replacement of the C-4 hydroxyl group, d. inducing an elimination reaction by base treatment to form a double bond between C-4 and C-5, e. removing the O-protecting group, f. removing the N-protecting group.

2. A compound of Formula III obtainable by step (a) of the method of claim 1:

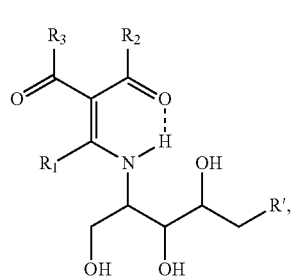

Formula III wherein

R' is as defined in claim 1,

R$_1$ is selected from H, alkyl, substituted alkyl, aryl, substituted aryl,

R$_2$ and R$_3$ are independently selected from alkyl, aryl, substituted alkyl, substituted aryl, O-alkyl, substituted O-alkyl, O-aryl, substituted O-aryl, NH$_2$, NHR", NR"R'", wherein R" and R'" are independently selected from the group consisting of alkyl and substituted alkyl, or might form a cyclic structure characterized by 5-8 ring sizes, and the dashed line ----- represents a hydrogen bond.

3. A compound of Formula IV obtainable by steps (a) to (b) of the method of claim 1:

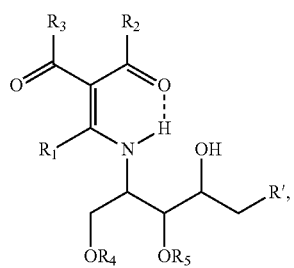

Formula IV wherein

R' is as defined in claim 1,

R$_1$ is selected from H, alkyl, substituted alkyl, aryl, substituted aryl,

R$_2$ and R$_3$ are independently selected from alkyl, aryl, substituted alkyl, substituted aryl, O-alkyl, substituted O-alkyl, O-aryl, substituted O-aryl, NH$_2$, NHR", NR"R'", wherein R" and R'" are independently selected from the group consisting of alkyl and substituted alkyl, or might form a cyclic structure characterized by 5-8 ring sizes, R$_4$ and R$_5$ are independently selected from optionally substituted benzyl, optionally substituted alkoxymethyl, trialkylsilyl, trialylsilyl or wherein R$_4$ and R$_5$ form a cyclic structure characterized by 5-8 ring sizes, and the dashed line ----- represents a hydrogen bond.

4. A compound of Formula V obtainable by steps (a) to (c) of the method of claim 1:

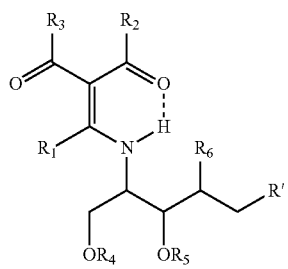

Formula V wherein
R', R$_1$, R$_2$, R$_3$, R$_4$ and R$_5$ are as defined in claim 1,
R' is as defined in claim 1,
R$_1$ is selected from H, alkyl, substituted alkyl, aryl, substituted aryl,
R$_2$ and R$_3$ are independently selected from alkyl, aryl, substituted alkyl, substituted aryl, O-alkyl, substituted O-alkyl, O-aryl, substituted O-aryl, NH$_2$, NHR", NR"R''', wherein R" and R''' are independently selected from the group consisting of alkyl and substituted alkyl, or might form a cyclic structure characterized by 5-8 ring sizes,
R$_4$ and R$_5$ are independently selected from optionally substituted benzyl, optionally substituted alkoxymethyl, trialkylsilyl, trialylsilyl or wherein R$_4$ and R$_5$ form a cyclic structure characterized by 5-8 ring sizes,
R$_6$ is a halide or a sulfonic ester,
and
the dashed line ----- represents a hydrogen bond.

5. The compound of Formula V according to claim 4, wherein R$_6$ is a halide selected from I, Br, Cl and Br.

6. The compound of Formula V according to claim 4, wherein R$_6$ is a sulfonic ester selected from mesylate (OMs), tosylate (OTs), triflate (OTf), nosylate (ONs), imidazole-1-sulfonate (OSO$_2$Im) and chlorophosphite ester (OPCl$_2$).

7. A compound of Formula VI obtainable by steps (a) to (d) of the method of claim 1:

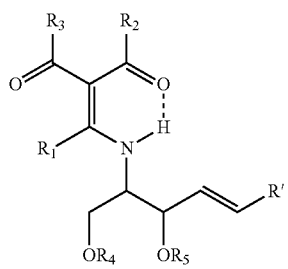

Formula VI wherein
R' is as defined in claim 1,
R$_1$ is selected from H, alkyl, substituted alkyl, aryl, substituted aryl,
R$_2$ and R$_3$ are independently selected from alkyl, aryl, substituted alkyl, substituted aryl, O-alkyl, substituted O-alkyl, O-aryl, substituted O-aryl, NH$_2$, NHR", NR"R''', wherein R" and R''' are independently selected from the group consisting of alkyl and substituted alkyl, or might form a cyclic structure characterized by 5-8 ring sizes,
R$_4$ and R$_5$ are independently selected from optionally substituted benzyl, optionally substituted alkoxymethyl, trialkylsilyl, trialylsilyl or wherein R$_4$ and R$_5$ form a cyclic structure characterized by 5-8 ring sizes,
and
the dashed line ----- represents a hydrogen bond.

8. A compound of Formula VII obtainable by steps (a) to (e) of the method of claim 1:

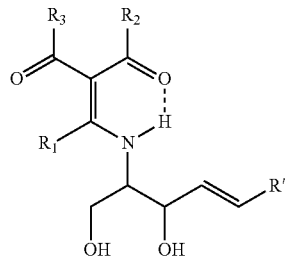

Formula VII wherein
R' is as defined in claim 1,
R$_1$ is selected from H, alkyl, substituted alkyl, aryl, substituted aryl,
R$_2$ and R$_3$ are independently selected from alkyl, aryl, substituted alkyl, substituted aryl, O-alkyl, substituted O-alkyl, O-aryl, substituted O-aryl, NH$_2$, NHR", NR"R''', wherein R" and R''' are independently selected from the group consisting of alkyl and substituted alkyl, or might form a cyclic structure characterized by 5-8 ring sizes,
and
the dashed line ----- represents a hydrogen bond.

9. A compound according to the method of claim 1, wherein the stereochemical configuration of the Formula equals the stereochemical configuration of D-erythro-sphingosine (2S,3R,4E) and of D-ribo-phytosphingosine (2S,3S,4R), respectively.

10. The method according to claim 1, wherein the vinylogous amide-type N-protecting group is 1,3-dimethyl-5-[(dimethylamino)methylene]-2,4,6(1H,3H,5H)-trioxopyrimidin ("DTPM").

11. The method according to claim 1, wherein the O-protecting group is an optionally substituted cyclic acetal or optionally substituted cyclic ketal.

12. The method according to claim 1, wherein the O-protecting group is optionally substituted benzylidene or optionally substituted isopropylidene.

13. A method for producing a sphingolipid, comprising:
N-acylation of a compound of Formulae III

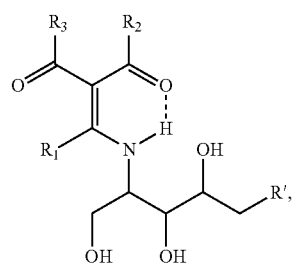

Formula III wherein
R' is H, aryl or an alkyl chain having 1-43 carbon atoms, which may be a straight chain or branched, and/or which may be saturated or contain one or more double bonds, and/or which may contain one or more functional groups, the functional group being selected from the group consisting of a hydroxyl group, an alkoxy group, a primary, secondary or tertiary amine, a thiol group, a thioether and a phosphorus containing functional group $R_1$ is selected from H, alkyl, substituted alkyl, aryl, substituted aryl, $R_2$ and $R_3$ are independently selected from alkyl, aryl, substituted alkyl, substituted aryl, O-alkyl, substituted O-alkyl, O-aryl, substituted O-aryl, $NH_2$, $NHR''$, $NR''R'''$, wherein $R''$ and $R'''$ are independently selected from the group consisting of alkyl and substituted alkyl, or might form a cyclic structure characterized by 5-8 ring sizes, and the dashed line ----- represents a hydrogen bond, using an acyl moiety of a $C_{12}$-$C_{30}$ acyl group which can be saturated, unsaturated or optionally substituted via the use of the corresponding carboxylic acid, acid chloride, ester or anhydride in the presence of an organic base.

\* \* \* \* \*